United States Patent [19]

Golec, Jr.

[11] Patent Number: 4,762,945
[45] Date of Patent: Aug. 9, 1988

[54] PROCESS FOR THE PREPARATION OF ASPIRIN PEROXIDE

[75] Inventor: Frederick A. Golec, Jr., Ossining, N.Y.

[73] Assignee: USV Pharmaceutical Corporation, Fort Washington, Pa.

[21] Appl. No.: 775,272

[22] Filed: Sep. 12, 1985

[51] Int. Cl.$^4$ ............................................ C07C 69/157
[52] U.S. Cl. .................................................... 560/138
[58] Field of Search ............... 560/138, 302; 568/566; 514/159

[56] References Cited

U.S. PATENT DOCUMENTS

| | | | |
|---|---|---|---|
| 3,435,060 | 3/1969 | Johannes | 560/302 |
| 3,849,468 | 11/1974 | Busseret | 560/302 X |
| 4,364,940 | 12/1982 | Neiss et al. | 514/533 |

*Primary Examiner*—Michael L. Shippen

[57] ABSTRACT

Process for preparing 2,2'-diacetoxy-dibenzoylperoxide by: reacting 2-acetyl-salicyloyl chloride with aqueous hydrogen peroxide in a reaction mixture medium of tetrahydrofuran and dichloromethane in the presence of an organic base; separating a dichloromethane extract; diluting the dichloromethane extract with methanol and crystallizing the anhydrous product therefrom.

2 Claims, No Drawings

PROCESS FOR THE PREPARATION OF ASPIRIN PEROXIDE

BACKGROUND OF THE INVENTION

1. Field of the Invention

This invention relates to the synthesis of aspirin peroxide

2. Description of the Prior Art 2,2'-Diacetoxy-dibenzoyl-peroxide, commonly called aspirin peroxide, is a member of the chemical class of compounds known as acyl-salicyloyl peroxides described in Beilstein's Handbuch Der Organischen Chemie, Aweites Erganzungswerk, Die-literatur von 1920-1929 umfassend; Unfelder and Vanino, Pharm. Zeitung 47, 847 (1902); and Vanino, Herzer, Ar. 441(1924). In Beilstein the preparation of 2,2'-diacetoxy-dibenzoyl-peroxide is described by reacting 2-acetyl-salicyloyl chloride with aqueous 30% (w/w) hydrogen peroxide in acetone using pyridine as the organic base. The resulting product is recrystallized from benzene and has a m.p. of 109°–110° C. with decomposition.

U.S. Pat. No. 4,364,940 describes aspirin peroxide as having anti-bacterial activity and being useful in the treatment of acne. The process of making aspirin peroxide involves the use of a reaction mixture of 2-acetyl-salicyloyl chloride, aqueous 30% hydrogen peroxide in acetone, anhydrous sodium sulfate and sodium bicarbonate at a reaction temperature of 0° C.

It is well recognized by scientists in this field that organic peroxides, and particularly aspirin peroxide, are potentially hazardous compounds due to their thermal and mechanical instability. For example, the use of acetone as a reaction medium is rather undesirable due to the possible formation of trace amounts of 2,2-dihydroperoxy propane which is shock sensitive. In addition, during the removal of acetone for the purpose of concentrating the organic peroxide, pockets of concentrated acetone solutions are formed containing peroxide impurities which are inherently unstable towards rapid decomposition and explosion. In any process for the synthesis of these materials this potential hazard must be acknowledged in order to provide a method which is both chemically efficient in terms of yield and quality of products, as well as technologically practical and feasible in terms of handling and operations. Futhermore, conventional synthetic methods for the preparation of organic peroxides, such as dibenzoyl peroxide, are not suitable for the synthesis of aspirin peroxide for the reasons that hydrolysis of the 2-acetoxy group in aspirin peroxide would occur resulting in hazardous, potentially detonating conditions in addition to low yields and the presence of unacceptably high levels of impurities.

A safe, efficient synthetic method for the preparation of 2,2'-diacetoxy-dibenzoyl-peroxide has been discovered in which the hazards associated with thermal and mechanical instability of the reactants and product are minimized resulting in a high product yield of from 36 to 45% and of at least 95% purity.

SUMMARY OF THE INVENTION

In accordance with the present invention, a synthetic method for producing 2,2'-diacetoxy-dibenzoyl-peroxide is provided comprising the steps of:

(1) preparing a reaction mixture medium consisting of:

a, the water miscible solvent, tetrahydrofuran; and
b, the water immiscible co-solvent, dichloromethane;

(2) maintaining the temperature of the reaction mixture medium below 5° C., and preferably at about 0° C. when adding to and dissolving in the reaction mixture medium 2-acetyl-salicyloyl chloride;

(3) adding an orgainc base, such as pyridine or an inorganic base, such as sodium carbonate, potassium carbonate or calcium hydroxide to the reaction mixture medium;

(4) adding, while maintaining the temperature of said medium below 5° C., of 50% w/w to 80% w/w, and preferably about 70% w/w, aqueous hydrogen peroxide to form a reaction mixture;

(5) causing a reaction to form 2,2'-diacetoxy-dibenzoyl-peroxide by maintaining the temperature at 5° C. to 10° C. and stirring said reaction mixture for at least 3 hours but not longer than 10 hours;

(6) partitioning the reaction mixture with ice water to form and retain a dichloromethane extract;

(7) diluting the extract with methanol;

(8) crystallizing the anhydrous 2,2'-diacetoxy-dibenzoyl-peroxide product from said extract; and (9) collecting said product by vacuum filtration.

To provide for thermal and mechanical stability, the anhydrous 2,2'-diacetoxy-dibenzoyl-peroxide is dissolved in acetone that is cooled to 0°–10° C. This solution is rapidly poured into ice-water while being vigorously stirred to precipitate hydrous 2,2'-diacetoxy-dibenzoyl-peroxide. The hydrous product can be stored safely and used for pharmaceutical/cosmetic applications.

DETAILED DESCRIPTION OF THE INVENTION

In accordance with the present invention of preparing anhydrous aspirin peroxide, the reaction mixture medium consists of tetrahydrofuron/dichloromethane in a ratio of about 1:4 v/v. It is preferred to have about 1 part of 2-acetyl-salicyloyl chloride in about 6.25 parts of tetrahydrofuron/dichloromethane. It is also preferable to use one molar equivalent of about 70% w/w hydrogen peroxide to two molar equivalents of 2-acetyl-salicyloyl chloride, along with 1.5 to 2.0 molar equivalents of a dibasic inorganic base (i.e. sodium carbonate, potassium carbonate or calcium carbonate) or 2 to 3 molar equivalents of an organic base, such as pyridine. Upon completion of the reaction, the preferred process is to partition the reaction mixture with about 2 to 5 volumes of ice water to cause separation of the dichloromethane extract that contains the product, aspirin peroxide. The dichloromethane extract is diluted with ethanol, isopropanol or, preferably, methanol in a ratio of about 1:2 v/v. The concentration of aspirin peroxide is then about 3–5% w/w, which allows optimum crystallization of the same from the dichloromethane/alcohol mixture.

The optimum conditions for the preparation of hydrous aspirin peroxide require dissolution of freshly prepared anhydrous aspirin peroxide in acetone at a temperature of about 0° to 10° C. to form a 4 to 6% w/w solution, followed by precipitation into about 1 to 4 volumes of ice water. The precipitated hydrous aspirin peroxide is separated by filtration or centrifugation and stored in "wet" condition. Water concentration of the hydrous product so obtained is about 20 to 50% w/w.

The above-described procedure successfully addresses the problems of the prior art. To wit: the combination of tetrahydrofuron and dichloromethane is a safe reaction mixture medium even when used with high strength hydrogen peroxide; and the process requires no concentration or removal of solvents to isolate the desired product.

The present invention will be further illustrated by the examples that follow. The starting materials/reactants used in said examples are known in the art and are commercially available.

EXAMPLE 1

Preparation of 2,2'-Diacetoxy-Dibenzoyl-Peroxide Anhydrous

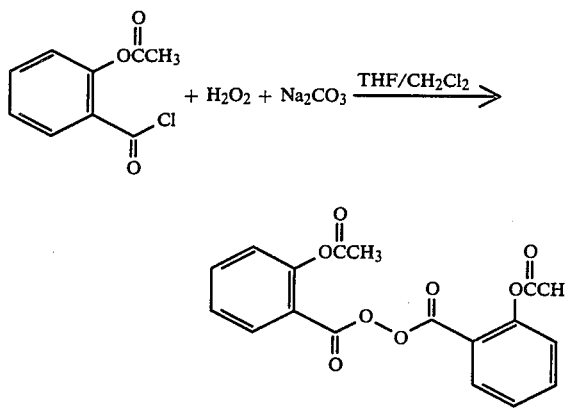

To a solution of 928 g (700 ml) of dichloromethane 155 g (175 ml) of tetrahydrofuran and 175.2 g (882.2 mmol) of 2-acetyl-salicyloyl chloride cooled in an ice bath was added 186.9 g (1.9 mol) of solid sodium carbonate.

The temperature was maintained below 5° C. during the addition of 21.3 g (438.6 mmol) of 70% (w/w) aqueous hydrogen peroxide.

After stirring for 8 hours at about 5° C.–10° C. the reaction mixture was partitioned with 2.0 kg of ice water.

The lower dichloromethane extract was removed and diluted with 1.1 kg (1.4 L) of methanol.

The product, 2,2'-diacetoxy-dibenzoyl-peroxide anhydrous, crystallized from the cold solution to yield 54.0 g of pure material.

EXAMPLE 2

Preparation of 2,2'-Diacetoxy-Dibenzoyl-Peroxide, Hydrous

The product, 2,2'-diacetoxy-dibenzoyl-peroxide, anhydrous (54 g) of Example 1 is dissolved in 1.0 L of acetone cooled to 0° C.

This solution is rapidly poured into 4.2 L of ice-water with vigorous stirring to precipitate 88 g of 2,2'-diacetoxy-dibenzoyl-peroxide, hydrous. The product was collected by vacuum filtration and contained less than 41% (w/w) of water.

EXAMPLE 3

Preparation of 2,2'-Diacetoxy-Dibenzoyl-Peroxide

Combined 19.8 g (100 mmols) of 2-acetyl-salicyloyl chloride and 7.2 g (52.4 mmols) of potassium carbonate in 106 g (80 ml) of dichloromethane and 17.7 g (20 ml) of tetrahydrofuran which was cooled at 5° C.

Added 2.54 g (52.4 mmols) of 70% w/w of aqueous hydrogen peroxide all at once.

The reaction mixture was then stirred at 5°–10° C. for 7 hours.

The reaction mixture was then partitioned with 400 ml of 1N sodium hydroxide solution.

The lower dichloromethane layer was then removed and diluted with 130 g (160 ml) of methanol and the product crystallized at 5° C.

The product was collected by suction filtration and had a weight of 6.5 g (38% theoretical yield) and assayed by titration analysis as 93% pure, analytical HPLC 97% pure.

EXAMPLE 4

Preparation of 2,2'-Diacetoxy-Dibenzoyl-Peroxide

Combined 19.8 (100 mmols) of 2-acetyl-salicyloyl chloride and 11.2 g (106 mmols) of sodium carbonate in 106 g (80 ml) of dichloromethane and 17.7 g (20 ml) of tetrahydrofuran which was cooled at 5° C.

Added 2.54 g (52.4 mmols) of 70% w/w of aqueous hydrogen peroxide dropwise over ca. 2 minutes. The reaction mixture was then stirred at 5° C. for 8¾ hours.

The reaction mixture was then partitioned with 400 g of ice water.

The lower dichloromethane layer was separated and partitioned with 100 ml of 5% aqueous sodium hydroxide solution.

The lower dichloromethane layer was separated and diluted with 130 g (160 ml) of methanol and the product crystallized at 5° C.

The product was collected by suction filtration and had a weight of 7.8 g (45% theoretical yield), and assayed by titration analysis as 97.1% pure, analytical HPLC 96.04% pure.

EXAMPLE 5

Preparation of 2,2'-Diacetoxy-Dibenzoyl-Peroxide

Combined 19.8 g (100 mmols) of 2-acetyl-salicyloyl chloride in 106 g (80 ml) of dichloromethane and 17.7 (20 ml) of tetrahydrofuran which was cooled to 5° C. Added 8.3 g (8.5 ml) (100 mmols) of pyridine dropwise to maintain the temperature below 15° C. The addition was strongly exothermic.

Cooled to 5° C. and added 2.5 g (52.4 mmols) of 70% w/w of aqueous hydrogen peroxide dropwise to maintain the temperature below 15° C. The addition was strongly exothermic.

Cooled to 5° C. and continued the reaction for 2¾ hours.

The reaction was then partitioned with 400 g of ice water and the lower dichloromethane layer removed.

The dichloromethane layer was then partitioned with 100 ml of ice cold 1N sodium hydroxide solution.

The lower dichlormethane layer was then removed and diluted with 130 g (160 ml) of methanol and the product crystallized at 5° C.

The product was collected by suction filtration and had a weight of 6.28 g (36% theoretical yield) and assayed by titration analysis as 96.4% pure, analytical HPLC 97% pure.

The process of the present invention results in 36% to 45% of theoretical yield and at least 95% purity. Trace impurities of less than 2% aspirin and less then 1% salicylic acid were confirmed by analytical testing. Stability studies of the hydrous product showed no apparent degradation after several months of storage.

What is claimed is:

1. A process for preparing anhydrous 2,2'-diacetoxy-dibenzoyl-peroxide comprising the steps of:
   (1) preparing a reaction mixture medium consisting of about 1 part by volume of tetrahydrofuran and about 4 parts by volume of dichloromethane;
   (2) while maintaining the temperature of the reaction mixture medium below 5° C., dissolving in said reaction mixture medium 2-acetyl-salicyloyl chloride, adding a base selected from the group consisting of pyridine, sodium carbonate, potassium carbonate and calcium hydroxide to said reaction mixture medium, and adding of 50% w/w to 80% w/w aqueous hydrogen peroxide;
   (3) causing a reaction between said 2-acetyl-salicyloyl chloride and said aqueous hydrogen peroxide to form 2,2'-diacetoxy-dibenzoyl-peroxide by maintaining the temperature of said reaction mixture at 5° C. to 10° C. for at least three hours but not longer than ten hours;
   (4) partitioning the reaction mixture with ice water to form and retain a dichloromethane extract;
   (5) diluting the dichloromethane extract with methanol; and
   (6) crystallizing the anhydrous 2,2'-diacetoxy-dibenzoyl-peroxide from said extract.

2. A process for preparing a stable hydrous 2,2'-diacetoxy-dibenzoyl-peroxide comprising the steps of:
   dissolving the anhydrous 2,2'-diacetoxy-dibenzoyl-peroxide immediately after the same has been crystallized in the last step of the process claimed in claim 1 in acetone, said acetone being maintained at a temperature of 0° C. to 10° C.;
   admixing said solution with ice-water and precipitating therefrom hydrous 2,2'-diacetoxy-dibenzoyl-peroxide.

* * * * *